US00PP20687P2

(12) United States Plant Patent van Noor

(10) Patent No.: US PP20,687 P2

(45) Date of Patent: Jan. 26, 2010

(54) *ECHINACEA* PLANT NAMED 'HOT SUMMER'

(50) Latin Name: ***Echinacea* hybrid**
Varietal Denomination: Hot Summer

(76) Inventor: Marco van Noor, Wasbeeklaan 13, 2361 HG Warmond (NL)

( * ) Notice: Subject to any disclaimer, the term of this patent is extended or adjusted under 35 U.S.C. 154(b) by 0 days.

(21) Appl. No.: 12/313,803

(22) Filed: Nov. 25, 2008

(51) Int. Cl.
*A01H 5/00* (2006.01)

(52) U.S. Cl. ..... Plt./428

(58) Field of Classification Search ..... Plt./263, Plt./428

See application file for complete search history.

*Primary Examiner*—Susan B McCormick Ewoldt
(74) *Attorney, Agent, or Firm*—Penny J. Aguirre

(57) ABSTRACT

A new cultivar of hybrid *Echinacea*, 'Hot Summer', characterized by its inflorescences with ray florets that emerge orange-red in color and mature to a deep red, its strong upright habit with blooms and plant habit maintained under environmental stresses such as heavy rains and wind, and its resistance to viral diseases.

3 Drawing Sheets

Botanical classification: *Echinacea* hybrid.
Variety denomination: 'Hot Summer'.

BACKGROUND OF THE INVENTION

The present Invention relates to a new and distinct cultivar of *Echinacea* of hybrid origin and will be referred to hereafter by its cultivar name, 'Hot Summer'. 'Hot Summer' represents a new purple coneflower, an herbaceous perennial grown for landscape use.

The new cultivar arose from an ongoing breeding and selection program conducted by the Inventor in a designated field at his nursery in Warmond, The Netherlands. The Inventor discovered the new cultivar, 'Hot Summer', as a naturally occurring whole plant mutation in his trial field in summer of 2007. The parentage is unknown as the Inventor grows numerous cultivars and species of *Echinacea* in his trial bed, however the characteristics of 'Hot Summer' suggest both *Echinacea paradoxa* and *Echinacea purpurea* in its parentage.

Asexual reproduction of the new cultivar was first accomplished by in vitro propagation in Rijswijk, The Netherlands in 2008 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Hot Summer' from other cultivars of *Echinacea* known to the Inventor.

1. 'Hot Summer' exhibits composite inflorescences that emerge with ray florets that are orange-red in color and mature to a deep red.
2. 'Hot Summer' exhibits a strong upright habit with blooms and plant habit maintained under environmental stresses such as heavy rains and wind.
3. 'Hot Summer' has been shown to be more resistant to viruses than is typical for cultivars of *Echinacea*.

The new cultivar is unique from other cultivars of *Echinacea purpurea* known to the Inventor in the color of its ray florets. *Echinacea paradoxa* differs from 'Hot Summer' in having ray florets that are yellow in color. The closest comparison cultivar is *Echinacea* 'Tomato Soup' (U.S. Plant Pat. No. 19,427), 'Hot Summer' differs primarily from 'Tomato Soup' in having ray flowers that change from orange-red to red rather than from pink to red as observed for 'Tomato Soup'.

BRIEF DESCRIPTION OF THE DRAWING

The plants and plant parts in the accompanying photographs depict a one year-old plant of 'Hot Summer' as grown outdoors in a test garden in Warmond, The Netherlands.

The photograph in FIG. 1 provides a side view of 'Hot Summer' in bloom.

Figure 1:
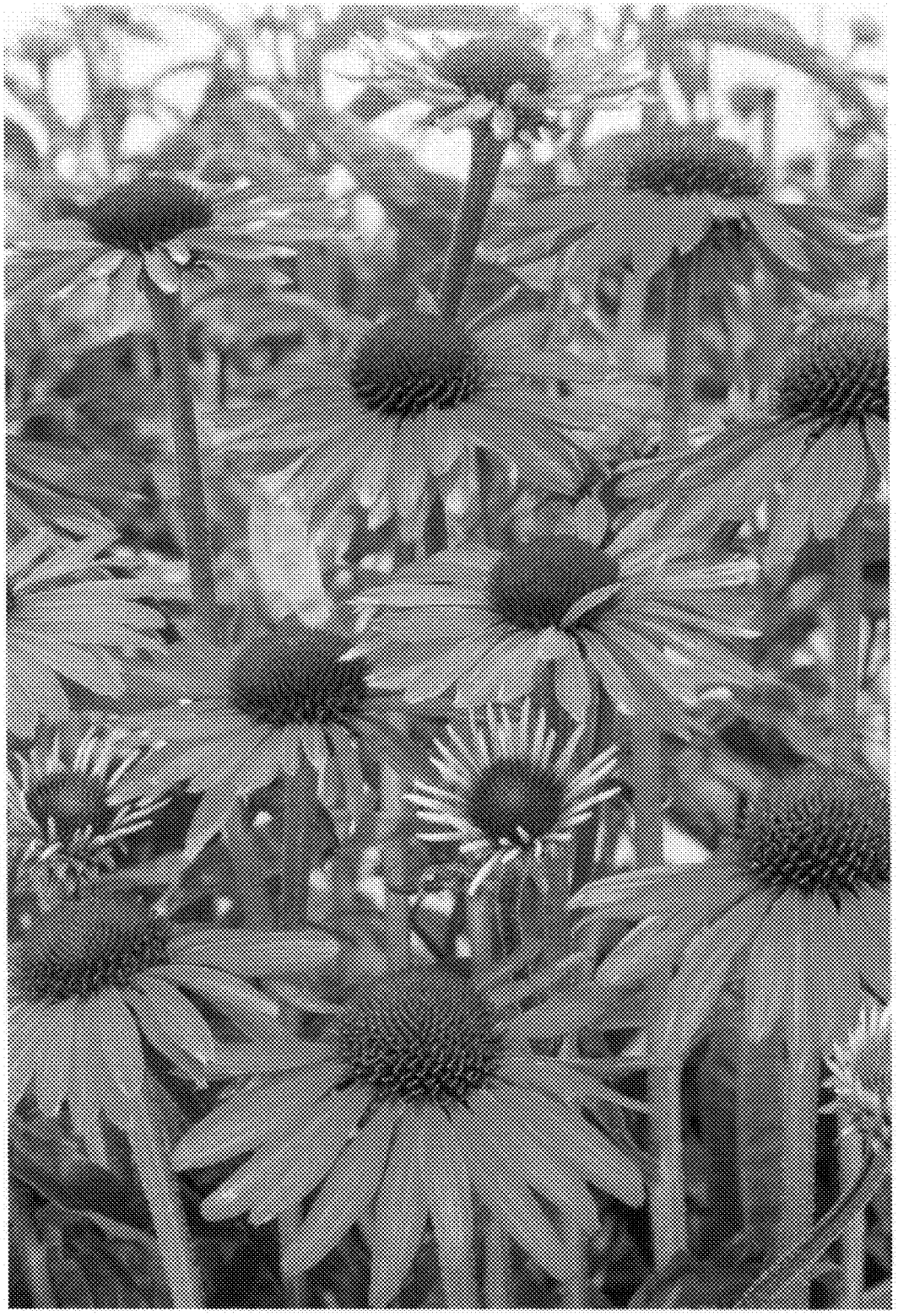
Figure 2:
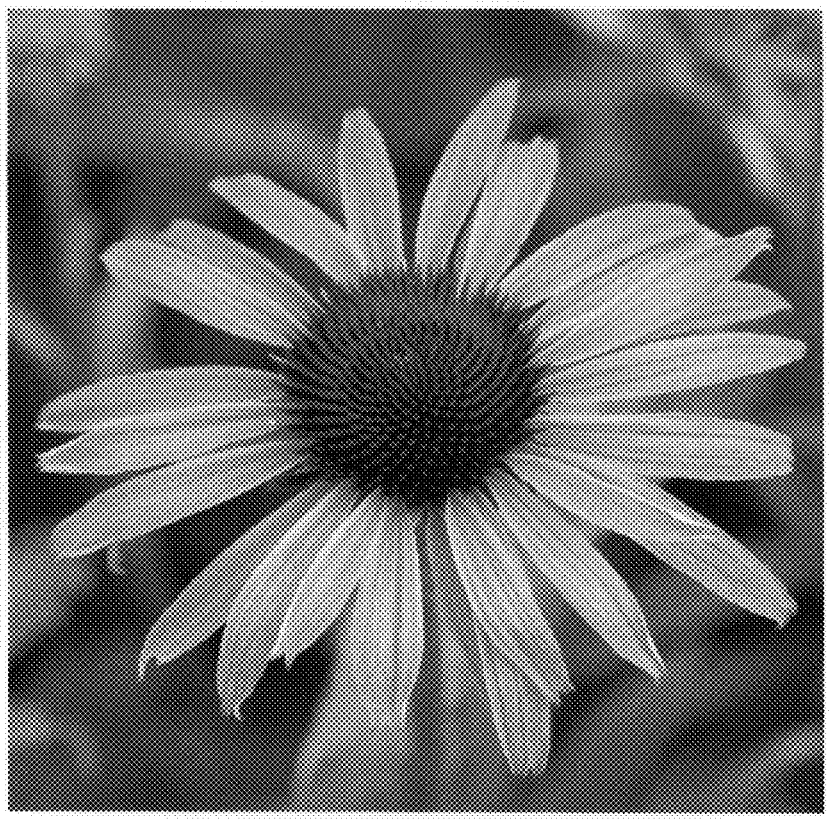

The photograph in FIG. 2 shows a close-up of an inflorescence of 'Hot Summer' that has just opened.

Figure 3:
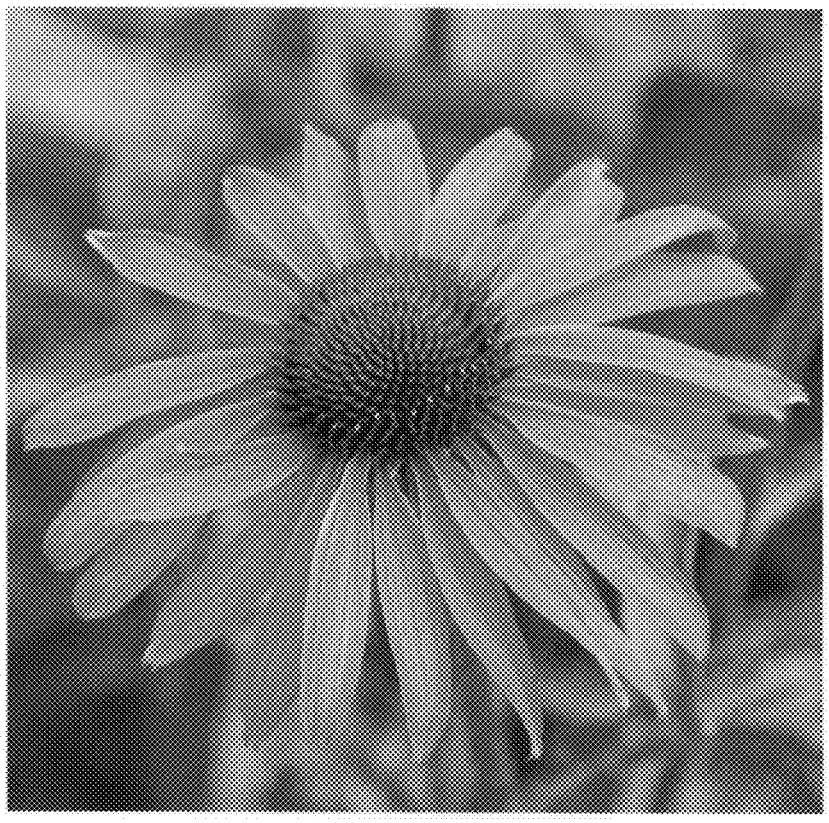

The photograph in FIG. 3 provides a close-up of an inflorescence of 'Hot Summer' that is maturing.

Figure 4:
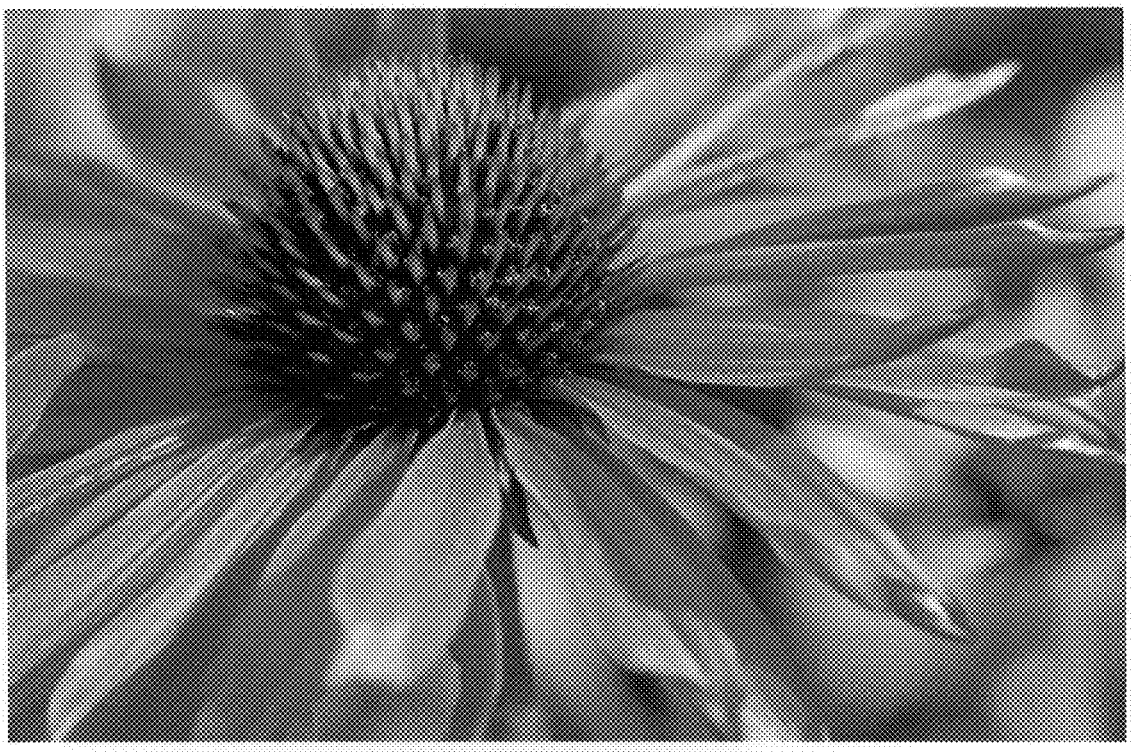

The photograph in FIG. 4 provides a close-up of an inflorescence of 'Hot Summer' that is fully mature.

Figure 5:
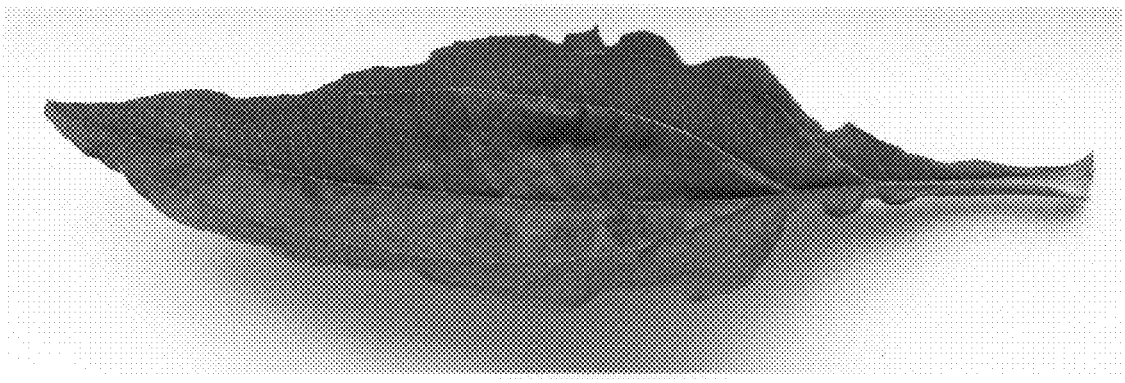

The photograph in FIG. 5 provides a close-up of a leaf of 'Hot Summer'.

The Colors in the photograph may differ slightly from the color values cited in the detailed botanical description, which accurately describe the colors of the new *Echinacea*.

BOTANICAL DESCRIPTION OF THE PLANT

The following is a detailed description of a one-year-old plant of the new cultivar as grown outdoors in a test garden in Warmond, The Netherlands. The plants were grown under average day temperatures of 12° to 32° C. and average night temperatures of 4° to 18° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Continuously from June to September.

*Plant habit.*—Herbaceous perennial, clump forming, upright.

*Height and spread.*—Reaches 70 to 90 cm in height and 30 to 40 cm in spread depending on soil fertility levels.

*Hardiness.*—At least in U.S.D.A. Zones 4 to 9.

*Diseases resistance.*—Has shown better resistance to viruses than is typical for many cultivars of *Echinacea.*

*Root description.*—Fibrous.

Growth and propagation:

*Propagation.*—Division, vegetative stem cuttings, and tissue culture.

*Growth rate.*—Moderate to highly vigorous.

Stem description:

*Shape.*—Slightly oval, solid.

*Stem color.*—146A to 146B.

*Stem size.*—Lateral stems are an average of 1 cm in diameter and an average of 38 cm in height excluding peduncles.

*Stem strength.*—Very strong.

*Stem aspect.*—Held upright.

*Stem surface.*—Moderately rough to touch and sparsely covered with short strigose hairs about 0.5 mm in length and 157D in color.

*Stem number.*—Average of 1 per one-year-old plant.

*Internode length.*—Average of 7.8 cm in length.

*Branching.*—Un-branched.

Foliage description:

*Leaf shape.*—Narrowly ovate.

*Leaf division.*—Simple.

*Leaf base.*—Attenuate.

*Leaf apex.*—Acute to narrowly acute.

*Leaf venation.*—Pinnate, 145B on upper and 146C to 146D on lower surface.

*Leaf margins.*—Irregularly dentate, undulating.

*Leaf attachment.*—Petiolate.

*Leaf arrangement.*—Alternate.

*Leaf size.*—Average of 16.9 cm in length and 7.3 cm in width.

*Leaf color.*—Newly formed upper surface; 137A, newly formed lower surface; 137B to 137C, mature upper surface; between 137A to 139A (closest to 137A), mature lower surface; 137B.

*Leaf surface.*—Upper surface is slightly glossy, lower surface is slightly glossy, both surfaces are moderately covered with short strigose hairs about 0.3 mm in length and 157D in color.

*Petioles.*—V-shaped, an average of 3.6 cm in length and 6 mm in width (petioles near top of stem are shorter), color upper surface; 145A to 145B in color with leafy margins 147A, color lower surface; 144B with leafy margins 137B, surface is covered with short strigose hairs about 0.3 mm in length and 157D in color.

Flower description:

*Type.*—Capitulum, heterogamous with ray florets around the head margin and disk florets in the center, forming a radiant head.

*Capitulum number.*—Average of 6 per stem.

*Lastingness of inflorescence.*—About 2 weeks.

*Capitulum size.*—Matures to about 5.9 cm in depth and 11.5 cm in diameter, disk is about 3.9 cm in diameter.

*Fragrance.*—Moderate, sweet-scented.

*Involucral bracts or phyllary.*—About 48 arranged in 3 overlapping rows, average of 1 cm in length and 3 mm in width, cuneate base, acute apex, narrowly ovate to lanceolate in shape, slightly curved towards peduncle, upper and lower surface is 137B to 137C in color, margins entire and densely covered with short strigose hairs about 0.3 mm in length and 157D in color, surface is smooth on both surfaces.

*Buds.*—Flatten globular in shape, up to 2.3 cm in diameter and 1.7 cm in height, color 150C with center 143B.

*Peduncle.*—Strong, terminal is an average of 35.1 cm in length and 6 mm in diameter with axillary peduncles an average of 30.1 cm in length and 6 mm in diameter, 144A in color, surface is rough to touch and sparsely covered with short strigose hairs about 0.5 mm in length and 157D in color.

*Ray florets* (*sterile*).—Average of 25 in single row, narrow elliptic to narrow Obovate in shape, vertical ridges on both surfaces, about 5.4 cm in length and 1.2 cm in width, emarginate to praemorse apex, cuneate base, entire margin except apex, smooth and dull surface on both surfaces, held horizontal when mature, color of upper surface when opening; 28A, color of lower surface when opening; 35C and 22B towards apex, color of upper surface when fully open; N34B and N34A to N34B towards apex, color of lower surface when fully open; 53C flushed in the center with 150D, color of upper surface when mature; 46A turning to 53B, color of lower surface when fully mature; 187D.

*Disk flowers* (*bisexual*).—Numerous, about 360, tubular in shape, fused into tube with upper 10% un-fused, arranged spirally on a triangular shaped receptacle, about 1.1 mm in height and 1.1 cm in width and 158D in color, apex is acute, fused base, entire margin, average of 1.1 cm in length and 2 mm in width, surface of upper surface and lower surface is smooth and slightly glossy, color when opening upper and lower surface; 146C to 146D with apex 178A, color of upper and lower surface when fully open; 146B to 146C with apex 178A.

*Disk spines.*—Average of 360, acicular in shape, acute apex, attenuate base, smooth and glossy surface, color is 33A at apex, 143B in mid region and 144C at base.

Reproductive organs (present on disk florets only):

*Gynoecium.*—Pistil; 1, 6.5 mm in length, style; about 8 mm in length and 187C to 187D in color, stigma; decurrent and N186C in color, ovary; 157D in color.

*Androcoecium.*—Stamens; 5, filaments; 2 mm in length and 145C in color, anthers; about 3 mm in length and 200A to 202A in color, pollen; moderate to high in quantity and 17A in color.

*Fruit/seed.*—No seed production has been observed.

It is claimed:

1. A new and distinct cultivar of *Echinacea* plant named 'Hot Summer' substantially as herein illustrated and described.

* * * * *